US012788029B2

(12) United States Patent
Spickermann et al.

(10) Patent No.: US 12,788,029 B2
(45) Date of Patent: Nov. 10, 2026

(54) FUNCTIONAL YEAST PROTEIN CONCENTRATE

(71) Applicant: OHLY GmbH, Hamburg (DE)

(72) Inventors: Dominik Spickermann, Hamburg (DE); Rovena Sieblitz, Hamburg (DE); Mathilde van Rheenen, Bremen (DE); Loi Gia Tu, Ahrensburg (DE); Catharina Kleist, Hamburg (DE); Cornelia Reimers, Hamburg (DE)

(73) Assignee: OHLY GmbH, Hamburg (DE)

( * ) Notice: Subject to any disclaimer, the term of this patent is extended or adjusted under 35 U.S.C. 154(b) by 0 days.

(21) Appl. No.: 19/098,773

(22) Filed: Apr. 2, 2025

(65) Prior Publication Data

US 2025/0228265 A1 Jul. 17, 2025

Related U.S. Application Data

(60) Continuation of application No. 19/049,542, filed on Feb. 10, 2025, now abandoned, which is a division of
(Continued)

(30) Foreign Application Priority Data

Dec. 21, 2018 (EP) .................................... 18215732

(51) Int. Cl.
*A23J 1/18* (2006.01)
*A23B 2/00* (2025.01)
(Continued)

(52) U.S. Cl.
CPC .................................... *A23J 1/18* (2013.01); *A23B 2/00* (2025.01); *A23J 3/20* (2013.01); *A23J 3/225* (2013.01);
(Continued)

(58) Field of Classification Search
CPC ...... A23J 1/18; A23J 3/20; A23J 3/225; A23J 3/227; A23B 2/00; A23L 5/51;
(Continued)

(56) References Cited

U.S. PATENT DOCUMENTS 3,848,812 A * 11/1974 Mogren .............. B02C 19/0056 426/656
3,867,255 A * 2/1975 Newell .................. C12N 1/005 435/921
(Continued)

FOREIGN PATENT DOCUMENTS

CN 101513247 A 8/2009
CN 106047739 A 10/2016
(Continued)

OTHER PUBLICATIONS

Translation of Cn 107519054A (Year: 2017).*
(Continued)

*Primary Examiner* — Drew E Becker
(74) *Attorney, Agent, or Firm* — Knobbe, Martens, Olson & Bear, LLP

(57) ABSTRACT

The present invention relates to a method for preparing a yeast protein concentrate, said method comprising the lysis of yeast cells in a suspension that was adjusted to a particular pH prior to lysis, subsequently subjecting the soluble fraction obtained from lysis to filtration to reduce the content of molecules smaller than 30 kDa, and optionally drying the solution obtained from filtration. The present invention further relates to a yeast protein concentrate obtainable by the method of the invention. The yeast protein concentrate comprises a high amount of proteins which are still folded and are therefore capable of aggregation to form a solid protein matrix upon heating. In addition, the yeast protein concentrate of the invention will be of unobtrusive taste and
(Continued)

is therefore particularly suited for use in the preparation of food items, such as meat substitute products.

18 Claims, 2 Drawing Sheets

Related U.S. Application Data application No. 17/416,290, filed as application No. PCT/EP2019/086646 on Dec. 20, 2019, now abandoned.

(51) Int. Cl.

| | |
|---|---|
| ***A23J 3/20*** | (2006.01) |
| ***A23J 3/22*** | (2006.01) |
| ***A23L 5/00*** | (2016.01) |
| ***A23L 31/10*** | (2016.01) |
| ***A23L 33/195*** | (2016.01) |
| ***C12N 1/063*** | (2026.01) |
| ***C12N 1/066*** | (2026.01) |

(52) U.S. Cl.

CPC ................. *A23L 5/51* (2016.08); *A23L 31/10* (2016.08); *A23L 33/195* (2016.08); *C12N 1/063* (2013.01); *C12N 1/066* (2013.01); *A23V 2002/00* (2013.01); *A23V 2250/546* (2013.01); *A23V 2300/10* (2013.01); *A23V 2300/18* (2013.01); *A23V 2300/24* (2013.01); *A23V 2300/31* (2013.01); *A23V 2300/50* (2013.01)

(58) Field of Classification Search

CPC ....... A23L 31/10; A23L 33/195; C12N 1/063; C12N 1/066; A23V 2250/546; A23V 2300/10; A23V 2300/18; A23V 2300/24; A23V 2300/31; A23V 2300/50; A23V 2200/262–264

See application file for complete search history.

(56) References Cited

U.S. PATENT DOCUMENTS

| | | | | | |
|---|---|---|---|---|---|
| 3,867,554 | A * | 2/1975 | Sucher | C12N 1/005 | 426/60 |
| 3,887,431 | A * | 6/1975 | Robbins | C12N 1/005 | 435/270 |
| 3,888,839 | A | 6/1975 | Newell et al. | | |
| 3,960,659 | A * | 6/1976 | Fazakerley | C12N 1/08 | 435/270 |
| 3,968,257 | A * | 7/1976 | Muller | C12N 1/16 | 435/255.4 |
| 3,991,215 | A * | 11/1976 | Robbins | A23J 1/18 | 435/921 |
| 3,996,104 | A * | 12/1976 | Lindblom | A23J 1/18 | 530/820 |
| 4,007,088 | A * | 2/1977 | Fencl | C12N 1/08 | 530/820 |
| 4,021,303 | A * | 5/1977 | Nakabayashi | A23J 1/18 | 435/942 |
| 4,079,048 | A | 3/1978 | Chao | | |
| 4,135,000 | A * | 1/1979 | Schuldt, Jr. | C12N 9/22 | 426/62 |
| 4,427,580 | A * | 1/1984 | Kinsella | C12Q 1/6806 | 530/358 |
| 4,559,307 | A | 12/1985 | Hopkins | | |
| 4,683,294 | A | 7/1987 | Van Wijnendaele et al. | | |
| 4,729,958 | A * | 3/1988 | Drozd | C12N 1/02 | 435/270 |
| 5,401,830 | A | 3/1995 | Mckenzie | | |
| 5,756,135 | A * | 5/1998 | Seeley | A23L 33/14 | 435/254.2 |
| 5,958,755 | A * | 9/1999 | Skelton | A23L 31/00 | 426/62 |
| 6,531,132 | B1 * | 3/2003 | Paufique | C12N 1/063 | 424/78.02 |
| 7,387,884 | B2 | 6/2008 | Suzuki et al. | | |
| 11,051,532 | B2 * | 7/2021 | Henderson, Jr. | A23C 20/00 | |
| 2004/0137560 | A1 * | 7/2004 | Suzuki | C12P 21/02 | 435/68.1 |
| 2008/0187988 | A1 | 8/2008 | Warmington et al. | | |
| 2014/0308430 | A1 | 10/2014 | Ason et al. | | |
| 2015/0024451 | A1 * | 1/2015 | Williams et al. | C07C 29/86 | 435/165 |
| 2015/0064308 | A1 | 3/2015 | Williams | | |
| 2017/0137477 | A1 * | 5/2017 | Patinier | C07K 1/14 | |
| 2017/0339979 | A1 | 11/2017 | Lecocq et al. | | |
| 2019/0329148 | A1 | 10/2019 | Schwenzow et al. | | |
| 2020/0397021 | A1 | 12/2020 | Henderson et al. | | |
| 2021/0267230 | A1 | 9/2021 | Menin et al. | | |
| 2022/0071231 | A1 | 3/2022 | Spickermann et al. | | |
| 2023/0389568 | A1 * | 12/2023 | Suarez Garcia | C12N 1/066 | |
| 2024/0057652 | A1 * | 2/2024 | Hwang | A23G 9/38 | |
| 2025/0204550 | A1 * | 6/2025 | Garcia | C12N 1/063 | |

FOREIGN PATENT DOCUMENTS

| | | | | |
|---|---|---|---|---|
| EP | 3898933 | B1 | 9/2025 | |
| GB | 1460030 | A | 12/1976 | |
| JP | S49-132268 | A | 12/1974 | |
| JP | S51-63992 | A | 6/1976 | |
| JP | S53-145985 | A | 12/1978 | |
| JP | 2002-209598 | A | 7/2002 | |
| JP | 2011-152058 | A | 8/2011 | |
| WO | WO 96/38057 | A1 | 12/1996 | |
| WO | WO-2012049504 | A1 * | 4/2012 | A23K 10/10 |
| WO | WO 2020/127951 | A2 | 6/2020 | |

OTHER PUBLICATIONS

Translation of NO 750380L (Year: 1975).*

Database WPI, Thomson Scientific, XP002797911, 2017.

McCormick, et al., "Baker's yeast—world's oldest food—is newest source of protein and other ingredients", Food Product Development, Magazines For Industry, New York, 1973, 7(6), pp. 17-20.

Extended Search Report in corresponding European Patent Application Serial No. 18215732.1, dated Jun. 13, 2019.

International Search Report and Written Opinion in corresponding PCT/EP2019/086646, dated Jul. 27, 2020.

Pacheco et al., "Hydrophilic and Rheological Properties of Brewer's Yeast Protein Concentrates", Journal of Food Science, 63 (2), pp. 238-243, Jun. 28, 2008 (Jun. 28, 2008).

Dunn, B. and Wobbe, C.R., 1992, Preparation of Protein Extracts from Yeast, Current Protocols in Molecular Biology, Unit13.13: 13.13.1-13.13.9.

Gibbons, L et al., 2014, Bead Beating: A Primer; Random Primers, 12: 1-20.

Henriques, M. et al., 2017, Liquid whey protein concentrates produced by ultrafiltration as primary raw materials for thermal dairy gels, Food Technol. Biotechnol. 55(4):454-463.

Liu, D. et al., 2016, Yeast cell disruption strategies for recovery of intracellular bioactive compounds—A review; Innovative Food Science and Emerging Technologies 36: 181-192.

Pacheco, M. and Sgarbieri, V., 1998, Hydrophilic and rheological properties of Brewer's Yeast Protein Concentrates, Journal of Food Science, 63(2): 238-243.

Pancrazio, G. et al., 2016, Spent brewer's yeast extract as an ingredient in cooked hams; Meat Science, 121: 382-389.

Sahlan, M., et al., 2018, Extraction and characterization of yeast extract bioethanol by product from empty palm oil bunch for raw material of cosmetic products, E3S Web of Conferences 67, 03040: 1-4.

Sample Preparation Product Guide, Merck Millipore, 2014: 1-8.

Van Reis, R. and Zydney, A., 2001, Membrane separations in biotechnology, Current Opinion in Biotechnology, 12: 208-2011.

(56) References Cited

OTHER PUBLICATIONS

Vieira, E. et al., 2013, Evaluation of brewer's spent yeast to produce flavor enhancer nucleotides: Influence of serial repitching, Journal of Agricultural and Food Chemistry, 61: 8724-8729 (Vieira et al., 2013).
Vieira, E. et al., 2016, Nutritive value, antioxidant activity and phenolic compound profile of brewer's spent yeast extract, Journal of Food Composition and Analysis, 52: 44-51; http:/ix.dol.Org/10.1016/j.jica.2016.07.006 (Vieira et al.,2016).
Zumstein, L., 1998, Dialysis and Ultrafiltration; Current Protocols in Molecular Biology, Appendix 3C: A.3C.1-A.3C.7.
XP-0027916863, DB accession No. 2016-701962. Originally Published Jun. 29, 2016.

* cited by examiner

FUNCTIONAL YEAST PROTEIN CONCENTRATE

CROSS-REFERENCE TO RELATED APPLICATION

This application is a continuation of U.S. application Ser. No. 19/049,542, entitled FUNCTIONAL YEAST PROTEIN CONCENTRATE, filed Feb. 10, 2025, which is a divisional of Ser. No. 17/416,290, filed on Jun. 18, 2021, and which claims priority to PCT Application No. PCT/EP2019/086646 filed on Dec. 20, 2019, and published in English as WO 2020/127951 on Jun. 25, 2020, which claims priority to EP application Ser. No. 18/215,732.1, filed on Dec. 21, 2018, each of which is incorporated by reference herein in their entirety.

BACKGROUND OF THE INVENTION

The present invention relates to a method for preparing a yeast protein concentrate, said method comprising the lysis of yeast cells in a suspension that was adjusted to a particular pH prior to lysis, subsequently subjecting the soluble fraction obtained from lysis to filtration to reduce the content of molecules smaller than 30 kDa, and optionally drying the solution obtained filtration. The present invention further relates to a yeast protein concentrate obtainable by the method of the invention. The yeast protein concentrate comprises a high amount of proteins which are still folded and are therefore capable of aggregation to form a solid protein matrix upon heating. In addition, the yeast protein concentrate of the invention will be of unobtrusive taste and is therefore particularly suited for use in the preparation of food items, such as meat substitute products.

The World Health Organization (WHO) assumes that the world population will increase by one-third in 2050, thereby posing a huge problem to the food and agricultural industry. As a result from the increased population, it is predicted that global meat production will double its present level with severe consequences for the environment. Today already, the production of feed for livestock animals consumes about one-third of the world's total land area. Increasing demands of agricultural areas will lead to further destructions of rain forests and to the massive release of greenhouse gases.

There is hence an enormous need for food products which can be produced in a resource- and climate-friendly way. Specifically, as the production of meat is associated with a considerable waste of resources, the development of meat substitute products will be a key factor for coping with the growing world population. A number of different meat substitute products have been developed which are based on plant proteins. However, the production of proteins from plants like soya is generally laborious and time-consuming, as it requires growing the plants on agricultural crop land. Accordingly, there is still a need for alternative sources for proteins that can be used in the production of foods such as meat substitute products.

SUMMARY OF THE INVENTION

The present invention is based on the finding that protein concentrates obtained from yeast are capable of forming an extraordinary solid protein gel with a specific texture and high consistency. Since yeast cells do not require complex nutrients or growing conditions, they represent a particularly advantageous starting material for producing protein-enriched compositions that can be further used to prepare food products, and in particular meat substitute products. The protein concentrates of the present invention can be non-GMO, gluten-free and suitable for vegetarian and vegan diets, thereby satisfying a broad range of consumer requirements.

DETAILED DESCRIPTION OF THE INVENTION

Figure 1:
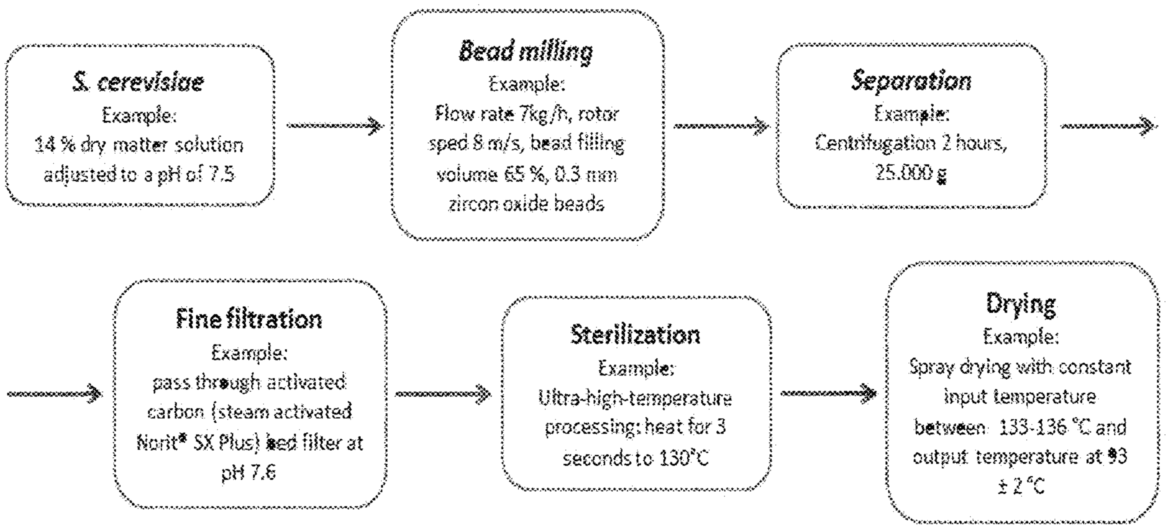
FIG. 1 shows a schematic overview of a preferred embodiment for preparing a yeast protein concentrate powder according to the invention.
Figure 2:
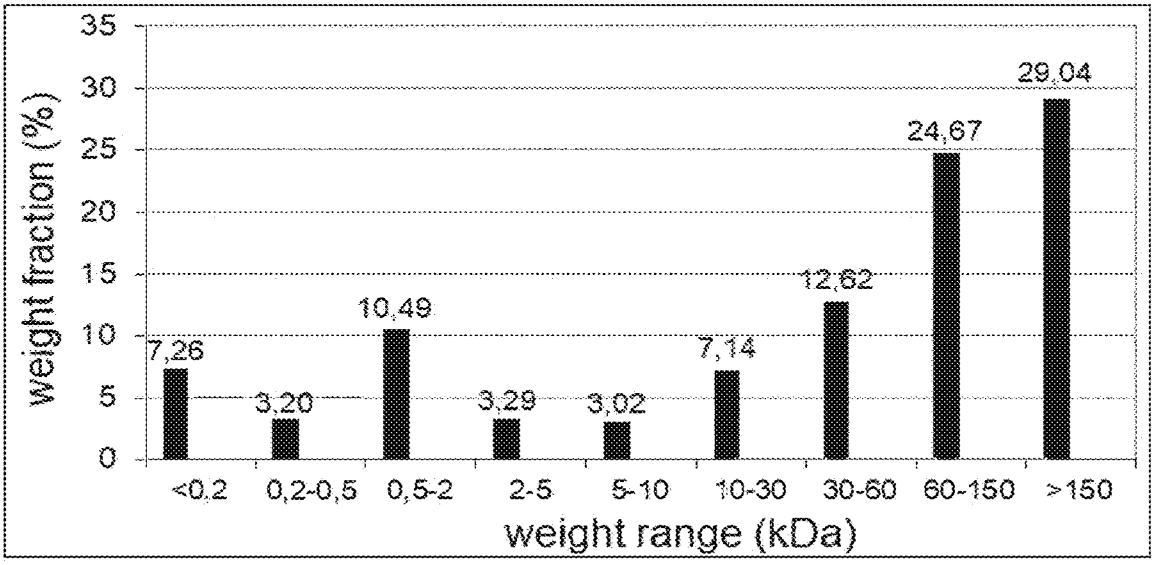
FIG. 2 shows the apparent molecular weight distribution of the proteins in a sample of the dried protein concentrate powder prepared in accordance with Example 1 described herein below.

In one aspect, the present invention rests on the insight that the firmness of a gel that is produced by heating a yeast protein concentrate can be modulated by adjusting the conditions applied during the production of the protein concentrate. In particular, it was found that the selection of an appropriate pH during the production of the concentrate strongly influences the gelling behavior of the final protein concentrate.

A protein concentrate produced in accordance with the method of the present invention is able to form a stable protein gel with a favorable consistency that resembles firm egg white. The present invention also provides a novel protein concentrate that can be used for preparing stable protein gels. The protein concentrate contains a high amount of proteins that have essentially maintained their structural integrity. This is achieved by preparing the concentrate under conditions that avoid the unfolding of the proteins. For example, the process is preferably conducted at temperatures that are low enough to avoid protein unfolding and, at the same time, diminish protease activity within the lysed yeast cell suspension.

The concentrates of the present invention can be liquids or dried powders. If the concentrate is provided in the form of a dried powder, it must be reconstituted with water for preparing a gel. When water is added to the powder, the proteins are solubilized and form a gel-like protein matrix upon heating to 50° C. or more. Since the taste of the yeast protein concentrate is unobtrusive, it can be mixed with different aromas to produce food items of different taste.

Thus, in a first aspect, the invention relates to a method for preparing a yeast protein concentrate comprising folded yeast protein molecules, said method comprising (a) providing a suspension comprising yeast cells;

(b) adjusting the pH of the suspension to a value between 6.5 and 8.5;

(c) lysing the yeast cells by mechanical means, preferably at a temperature of below 40° C.;

(d) subjecting the soluble fraction of the lysate to filtration to reduce the content of molecules smaller than 30 kDa; and (e) optionally, drying the solution obtained from filtration in step (d) to obtain a protein concentrate powder.

In the first step of the above method, a suspension comprising yeast cells is provided. In a simple embodiment, the suspension of yeast cells can be a fraction of cell-containing medium that was used for cultivating the yeast cells. This cell-containing medium can be directly used as a suspension in the sense of step (a) of the above method. Culture media and methods for growing yeast are well known in the art. Suitable media comprise, for example, the YPD medium of Sigma Aldrich (Taufkirchen, Germany).

In another embodiment, suspension used in step (a) is a suspension of yeast cells in water. For this purpose, the yeast cells are harvested after they have been grown to a certain density by separating the cells from the culture medium. For example, the cell-containing medium is subjected to centrifugation or separation in order to sediment the cells. Optionally, the cells may be washed with water or a suitable buffer to remove medium components. The cell pellets are subsequently re-suspended in water or a suitable buffer. The yeast cells which have been re-suspended in water or buffer then represent the yeast cell-containing suspension in step (a) of the above method.

Preferably, the cell suspension provided in step (a) of the above method has a volume of at least 100, at least 200, at least 300, at least 400, at least 500, at least 600, at least 700, at least 800, at least 900, at least 1,000, at least 5,000, or at least 10,000 liters. Preferably, the suspension is an aqueous suspension.

It is preferred that the yeast cell suspension provided in step (a) has been adjusted to have a dry matter content of between about 4-20%, preferably between about 5-16%, and even more preferably between about 6-14%, such as 12%. The dry matter percentages cited herein refer to wt. % based on the total weight of the suspension. The dry matter content of a suspension can be determined in accordance with standard procedures using commercially available devices, for example, the Moisture Analyzer (Mettler-Toledo GmbH, Gießen, Germany). Once the dry matter content of a starting suspension has been determined, this suspension can be adjusted to a pre-determined value either by diluting or concentrating the suspension.

The type of yeast that is used for preparing the protein concentrate of the invention is not specifically limited. Yeast cells which can be used for the method of the invention may comprise, for example, a yeast belonging to the genus *Saccharomyces*, such as *S. cerevisiae, S. chevalieri, S. boulardii, S. bayanus, S. italicus, S. delbrueckii, S. rosei, S. microellipsodes, S. carlsbergensis, S. bisporus, S. fermentati, S. rouxii, or S. uvarum*; a yeast belonging to the genus *Schizosaccharomyces*, such as *S. japonicus, S. kambucha, S. octosporus*, or *S. pombe*; a yeast belonging to the genus Hansenula, such as *H. wingei, H. arni, H. henricii, H. americana, H. canadiensis, H. capsulata, or H. polymorpha*; a yeast belonging to the genus *Candida*, such as *C. albicans, C. utilis, C. boidinii, C. stellatoidea, C. famata, C. tropicalis, C. glabrata*, or *C. parapsilosis*; a yeast belonging to the genus *Pichia*, such as *P. pastoris, P. kluyveri, P. polymorpha, P. barkeri, P. cactophila, P. rhodanensis, P. cecembensis, P. cephalocereana, P. eremophilia, P. fermentans*, or *P. kudriavzevii*; a yeast belonging to the genus *Kluyveromyces*, such as *K. marxianus*; and a yeast belonging to the genus *Torulopsis*, such as *T. bovina*, or *T. glabrata*.

In a particularly preferred embodiment, the method of the invention uses a suspension comprising yeast cells from the genus *Saccharomyces*, more preferably from *S. cerevisiae.*

In another particularly preferred embodiment of the invention, the cells are washed with an alkaline buffer, such as a sodium hydroxide buffer. Such washing step is useful to reduce the strong taste of the yeast suspension and therefore helps to achieve a final protein concentrate with an unobtrusive taste. If the method of the invention includes a washing step with an alkaline buffer, at least one subsequent washing step with water is included into the method to ensure that residual alkaline buffer is removed. For example, if the yeast suspension is washed with a certain volume of alkaline buffer, it s subsequently washed with twice the volume of water before lysis.

Prior to lysing the cells, the pH of the suspension is adjusted to a value between 6.5 and 8.5 in step (b) of the above method. For adjusting the pH, standard basic and acidic reagents, such as HCl and NaOH, can be used. It has been found that the pH in the range between 6.5 and 8.5 is surprisingly useful to improve the gelling behavior of the final protein concentrate. In a preferred embodiment, the pH of the yeast cells suspension is about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5. A pH between 7.0 and 8.0 or between 7.2 and 7.8, such as 7.5 is particularly preferred.

In another preferred embodiment of the invention, a ribonuclease (RNase) enzyme is added to the suspension immediately prior to cell lysis. It has been found that the addition of an RNase enzyme significantly improves the separation of soluble from insoluble matter after lysis. RNase enzymes can be obtained from different manufacturers. Suitable enzymes may include PureLink RNase A from Thermo Fisher Scientific (Bremen, Germany) or RNase A from Sigma Aldrich (Taufkirchen, Germany). A skilled person will have no problems to determine the optimum amount of the RNase enzyme to be added to the yeast cell suspension. Suitable amounts of the RNase enzyme will normally be in the range of about 0.1% to 1% per dry matter.

After the pH of the cell suspension has been adjusted, the yeast cells are lysed in step (c) of the above method to release the yeast proteins. Yeast species like *Saccharomyces cerevisiae* have a thick cell wall that determines its shape and protects its interior. The cell wall of yeasts mainly consists of β-glucans, mannoproteins, and chitin in a covalently linked matrix, and it comprises approximately one third of the total yeast dry matter. Beneath the cell wall, yeast cells have a lipid bilayer. To release proteins from the cell interior, both of these protective barriers need to be disrupted.

According to the method of the invention, cell lysis will be performed mechanically, because the use of proteases or other enzymes like e.g. glucanases, which are commonly employed for yeast cell lysis, would require elevated temperatures. That in turn would result in a rapid decomposition of the proteins. It is particularly important to control the temperature in this step. It has to be ensured that the temperature does not exceed 40° C., since higher temperatures would induce denaturation of the proteins, which means that the proteins would no longer be able to form a stable network upon heating. In addition, yeast cells contain a wide variety of proteases which are able to hydrolyze proteins into amino acids. When yeast cells are disrupted, the proteases are released and could decompose the other protein molecules which are released by the yeast cells.

Since the protein concentrates to be prepared by the method of the present invention are intended for use in human food products, the use of protease blockers, like EDTA or PMSF should be avoided, since these chemicals are not safe for use in human consumption. Accordingly, it is preferred according to the invention that the cell lysis is performed at low temperatures in order to reduce the activity of proteases.

It is preferred that steps (a)-(d) of the method of the invention are performed at temperatures of below 40° C., more preferably below 30° C., and even more preferably below 20° C. A temperature of below 20° C., such as 15° C. or 10° C., is particularly preferred to avoid an undesired decomposition of the proteins by proteases released from the yeast cells.

According to a preferred embodiment, yeast cell lysis is achieved by use of a bead mill. On the one hand, this ensures that the proteins remain intact upon cell rupture. On the other hand, the use of a bead mill does not require any additives that could impair the food grade quality of the resulting protein concentrates. A bead mill normally comprises a chamber that is filled with beads which are moved around by a set of impeller fins. When a cell-containing suspension is passed through the chamber, the cells are disrupted upon collision with the beads. The efficiency of cell rupture can be adjusted by routine measures, for example, by changing the flow rate which determines how fast the yeast suspension is passed through the chamber of the bead mill. Normally, a low flow rate leads to high lysis efficiency, since the cells have more time to collide with the grinding beads. Dependent on the volume of the chamber of the bead mill, flow rates of at least 10 kg/h can be selected, such at least 20 kg/h, at least 50 kg/h, or at least 100 kg/h. It is particularly preferred that during operation the bead mill is cooled to temperatures below 20° C., such 18° C., 16° C., 14° C., 12° C. or 10° C. Bead mills are offered by different manufacturers, for example, the Dyno®-Mill Multi Lab Wab from Willy A. Bachofen AG (Muttenz, Switzerland)

Another factor that has a direct impact on the efficiency of lysis is the bead material and size. Beads can be made of different materials, e.g. glass, ceramic or plastic. Particularly good results have been achieved with zirconium oxide beads, such as yttria-stabilized zirconium oxide beads. In addition, these beads are significantly more durable compared to glass beads. The beads used for disrupting the yeast cells, e.g. the zirconium oxide beads, may have different sizes which normally range from 0.2-2.0 mm. It has been found that for disrupting the yeast cells, a bead size of 0.25-0.35 mm leads to particularly good results. Accordingly a bead size of 0.25-0.35 mm is particular preferred. Bead filling volumes of between 30-80% may be used, for example, about 30%, about 35%, about 40%, about 45%, about 50%, about 55%, about 60%, about 65%, about 70%, or about 75%. A bead filling volume of between 50-60% is particularly preferred according to the invention.

Another way of influencing the efficiency of cell rupture is to adapt the impeller architecture. The impeller is normally mounted with plastic fins to move the beads. For improved cell rupture, it is for example possible to provide accelerators onto the rotor. Accelerators are designed to force the beads to collide more often. The impeller rotation speed is another parameter that may be adjusted to improve cell rupture. A rotor speed of between 1-20 m/s can be used, for example, about 1 m/s, about 2 m/s, about 3 m/s, about 4 m/s, about 5 m/s, about 6 m/s, about 7 m/s, about 8 m/s, about 9 m/s, about 10 m/s, about 11 m/s, about 12 m/s, about 13 m/s, about 14 m/s, or about 15 m/s. A skilled person would be readily able by routine experimentation to find optimum parameters for disrupting a yeast suspension in a bead mill.

Yet another way of mechanically lysing the yeast cells uses high-pressure homogenization (HPH). High pressure homogenization is a method commonly used in the pharmaceutical, chemical and food industry to stabilize emulsions, and the like. It can however also be used to disrupt bacteria and yeast in order to extract intracellular products from the cells. During HPH, the cells to be disrupted are passed through a narrow slit under high pressure. As the yeast cells pass this narrow slit, the flow rate sharply increases and the pressure abruptly decreases. The resulting shear forces cause cell disruption.

HPH devices for use in the method of the present invention can be obtained from different manufacturers. For example, the EmulsiFlex-C3 of Avestin Europe GmbH (Mannheim, Germany) or the 1000/2000 Homogenizer of SPX Flow Technology Germany GmbH (Moers, Germany) can be used. The yeast suspension can be passed through the HPH device one time or several times. If the suspension is passed through the device several times, the efficiency of cell rupture increases. The pressure of the device can be set to a pressure of at least 1000 bar. Preferably, the pressure will be at least 1100 bar, at least 1200 bar, at least 1300 bar, at least 1400 bar, at least 1500 bar, at least 1600 bar, at least 1700 bar, at least 1800 bar, at least 1900 bar, or at least 2000 bar or more.

After disrupting the cells as described above, the pH of the lysate may approach a value of 6.0 or below. It is preferred that the pH of the lysate is re-adjusted to a value between 6.5 and 8.5. For example, the pH of the lysate is re-adjusted to about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, or about 8.5. A pH between 7.0 and 8.0 or between 7.2 and 7.8, such as 7.5 is particularly preferred.

After the yeast cells have been disrupted, the soluble fraction containing, amongst other components, the folded yeast proteins is preferably separated from the insoluble fraction, the latter of which mainly contains cell wall components, cell organelles and unlysed cells. The separation of the soluble from the insoluble fraction can be performed by different methods, including centrifugation, filtration, and other methods. In a simple embodiment, the lysate containing the disrupted cells, either diluted or not, is subjected to centrifugation, for example, at 2,000-25, 000 g to sediment the insoluble matter. The supernatant containing the soluble cell components released from the cell interior, including the folded proteins, is obtained and preferably cooled to below 20° C. until further use.

Alternatively, the separation of the soluble and insoluble fractions is effected by a standard filtration technique using a filter material that retains insoluble matter. For example, a dead-end filtration using filters with pore sizes of 0.2-15 μm may be carried out. Also possible are cross flow or tangential flow filtrations to avoid premature blocking of the filter. The molecular weight cut off (MWCO) should be larger than 300 kDa to allow all the proteins to pass.

In step (d) of the above method, the soluble fraction of the lysate is subjected to filtration step that selectively reduces the content of molecules smaller than 30 kDa. Preferably, the content of molecules smaller than 30 kDa is reduced by at least 25%, more preferably at least 30%, at least 40%, at least 50%, at least 60%, at least 70%, at least 80%, at least 90%, or at least 95% relative to the content of these molecules in the soluble fraction of the lysate obtained in step (c) of the above method.

The molecules removed by the filtration step are preferably smaller than 20 kDa, more preferably smaller than 10 kDa and even preferably smaller than 5 kDa.

Suitable filtration methods for removing molecules smaller than 30 kDa are known and include, for example, activated carbon filtration, ultrafiltration, or nanofiltration. Activated carbon filtration is a separation method which is based on the adsorption of molecules to the surface of carbon particles and the entrapment of small molecules in indentations and pores of the activated carbon. For example, fluids may be passed through a filtration bed of activated carbon molecules and small organic molecules are bound by the carbon particles in the filtration bed. Alternatively, the activated carbon can be given directly to the fluids, incubated for a certain time with or without mixing, and subsequently removed from the carbon.

Alternatively or additionally, an ultrafiltration and/or nanofiltration can be used to remove molecules smaller than 30 kDa, preferably smaller than 20 kDa, more preferably smaller than 10 kDa and even preferably smaller than 5 kDa. These filtration techniques use membranes which act as a physical barrier having pores of a specific dimension. Both filtration techniques may be applied as dead end filtration or as tangential flow filtration. The membranes are designed to allow only particles having smaller diameters than the pore diameters to pass. During filtration, the initial solution is separated into two different fractions, the fraction that has passed the membrane (permeate) and the fraction that has been retained by the membrane (retentate). Filters used during ultrafiltration are usually defined by their molecular weight cut off (MWCO) that typically ranges from 0.1-1,000 kDa. In one embodiment, an ultrafiltration is carried out in step (d) of the above method using a membrane with a molecular weight cut off (MWCO) of 30 kDa or less, preferably 20 kDa or less, 10 kDa or less, and most preferably 5 kDa or less.

Optionally, the protein solution obtained after filtration is sterilized or pasteurized. It is preferred that the protein solution is sterilized or pasteurized without heating the product, e.g. by UV sterilization and the like. Alternatively, sterilization or pasteurized can be effected by subjecting the protein solution to very short ultra-high-temperature processing. For example, the protein solution can be heated to a temperature of 120-150° for 3-5 seconds.

The solution obtained after filtration step (d) is a liquid protein concentrate in the sense of the present invention. The liquid concentrate can be used for preparing gels. For this purpose, an aliquot of the concentrate is heated to a temperature of 50° C. or higher. The high temperature induces the proteins in the concentrate to unfold and to associate with each other, thereby forming gels.

The solution obtained after filtration step (d) may also be dried, thereby providing a protein concentrate powder. The powder has a significantly improved shelf life, since the proteins in the powder are no longer susceptible for decomposition by endogenous or exogenous proteases. A decomposition of the yeast proteins would lead to reduced gelling properties of the proteins concentrate. A further advantage is that the powder is protected from growth of microbial contaminants which could influence food safety. According to the invention, it is preferred that drying of the solution obtained from filtration is effected by freeze dying or spray drying.

The principle of spray drying is based on the dispersion of a solution into fine droplets which are introduced into a flow of hot air. The solvent evaporates from the substrate droplets so that dry product clusters remain. In the present case, it is important to select temperature conditions that do not lead to the denaturation of the proteins. Although spray drying is performed at temperatures that are normally higher than the melting temperature of proteins, this does not mean that the proteins completely unfold during spray drying. Protein denaturation is not an instant event, but instead is a process with many transition phases. Thus, by limiting the time periods of high temperatures during spray drying, denaturation of the yeast protein can be avoided. Standard spray drying devices can be used, such as the Mini Spray Dryer B-290 from Büchi Labortechnik GmbH (Essen, Germany) or the Mobile Minor™ Spray Dryer from GEA (Berlin, Germany).

Freeze drying or lyophilization is a process which removes water from a product to extend shelf life. Freeze drying encompasses freezing the product, reducing the pressure and adding heat to allow the frozen water in the material to sublimate. Various methods can be applied for freezing the product. For example, freezing can be achieved by using a standard freezer or a chilled bath. Cooling the product below its triple point ensures that sublimation will occur upon heating. To prevent the formation of large crystals that may damage the structure of the product to be dried, freezing is done rapidly. About 95% of the water in the product is removed when the frozen water sublimates. Most materials can be dried to 1-5% residual moisture. Standard freeze drying devices can be used, such as the Lyovac™ devices from GEA (Berlin, Germany), the Gamma 2-20 Freeze dryer LCM-1 from Christ (Osterode am Harz, Germany), or the Christ Martin™ Alpha 1-2 Lyophilisator from Fisher Scientific GmbH (Schwerte, Germany).

In another aspect, the invention provides a yeast protein concentrate obtainable by a method as described above.

In yet another aspect, the invention provides a yeast protein concentrate, either in the form of a liquid or powder, comprising a mixture of unfolded and folded proteins, wherein the folded proteins contained in the protein concentrate unfold at a temperature range between 45° C. and 83° C. The presence of folded proteins and their respective unfolding temperatures can be analyzed by a standard device for measuring protein stability and functionality, such as a Tycho NT.6 (NanoTemper Technologies GmbH, Munich). The Tycho NT.6 quantifies protein unfolding at increasing temperature by spectrometric measurement of light absorbance at 330 nm and 350 nm. The change in this ratio corresponds to protein unfolding. Where the sample contains a complex mixture of various proteins, there is no distinct melting temperature, but a melting range.

According to a preferred embodiment of the invention, at least 40% of the proteins contained in said concentrate have an apparent size of more than 5 kDa. Preferably, at least 50%, at least 60% or at least 70% of the proteins contained in the protein concentrate have an apparent size of more than 5 kDa.

According to another preferred embodiment of the invention, at least 40% of the proteins contained in the yeast protein concentrate have an apparent size of more than 10 kDa. Preferably, at least 50%, at least 60% or at least 70% of the proteins contained in the protein concentrate have an apparent size of more than 10 kDa.

According to another preferred embodiment of the invention, at least 40% of the proteins contained in the yeast protein concentrate have an apparent size of more than 20 kDa. Preferably, at least 50%, or at least 60% of the proteins contained in the protein concentrate have an apparent size of more than 20 kDa.

According to another preferred embodiment of the invention, at least 40% of the proteins contained in the yeast protein concentrate have an apparent size of more than 30 kDa. Preferably, at least 50%, or at least 60% of the proteins contained in the protein concentrate have an apparent size of more than 30 kDa.

According to another preferred embodiment of the invention, at least 30% of the proteins contained in the yeast protein concentrate have an apparent size of more than 60 kDa. Preferably, at least 40% of the proteins contained in the protein concentrate have an apparent size of more than 60 kDa.

According to another preferred embodiment of the invention, at least 20% of the proteins contained in the yeast protein concentrate have an apparent size of more than 150 kDa. Preferably, at least 25% of the proteins contained in the protein concentrate have an apparent size of more than 150 kDa.

It is further preferred according to the invention that the yeast protein concentrate of the invention contains less than 45% compounds which are not proteins. More preferably, the content of non-protein compounds in the protein concentrate is less than 40%, less than 35%, or less than 30%.

In addition, the protein concentrate of the invention has a particularly low amount of free amino acids and dipeptides or tripeptides. Preferably, the total amount of free amino acids, dipeptides and tripeptides is less than 20%, more preferably less than 18%.

The protein concentrate of the invention preferably have an RNA content of less than 15% (w/w), more preferably less than 14%, less than 13%, less than 12%, or less than 11%. The amount of free nucleotides preferably is less than 5% (w/w), more preferably less than 4%, less than 3%, or less than 2%.

In yet another aspect, the invention provides a yeast concentrate, either in the form of a liquid or powder, that comprises at least 55% (w/w), and preferably at least 60% (w/w), at least 65% (w/w), or at least 70% (w/w) total crude protein per dry matter, and wherein at least 40% of the proteins in the concentrate have a size of more than 60 kDa.

As used herein, the total crude protein content is preferably determined by measuring the nitrogen content of a sample by the commonly used Kjeldahl method and multiplying the result with the conversion factor 6.25. In other words, the total crude protein content is determined by the formula: Protein=Kjeldahl nitrogen content×6.25. In this context, the term "total crude protein" indicates that nitrogen-containing compounds other than proteins in the sample may to some extent contribute to this value, e.g. urea or free amino acids. The Kjeldahl method is widely known in the prior art as the most common procedure for determining the total crude protein content in a sample. Fully automated devices for determining the crude protein content by the Kjeldahl method are sold by several manufacturers, e.g. Kjeltec™ 8400 device (Foss GmbH, Hamburg, Germany).

As used herein, the concentrate of the invention comprises at least 55% (w/w) total crude protein per dry matter which means that 1.0 g of the concentrate, on a dry matter basis, comprises at least 0.55 g total crude protein. Dry matter refers to the weight of the completely dried compound. Preferably, the total crude protein is measured with a Kjeltec™ 8400 device.

In the concentrate that comprises the recited amount of at least 55% (w/w) total crude protein per dry matter, at least 40% of the proteins have an apparent size of more than 60 kDa. In other words, the concentrate of the invention comprises a high amount of larger proteins. The apparent size of the proteins in the concentrate can be measured by routine methods, such as size exclusion chromatography (SEC).

It is preferred that a yeast protein concentrate according to the present invention comprises 30% (w/w) or less, preferably 25% (w/w) or less, and more preferably 20% (w/w) or less beta-glucans per dry matter. In other words, 1.0 g of the concentrate, on a dry matter basis, comprises at best 0.3 g beta-glucans and preferably less.

In the protein concentrate that comprises at least 55% (w/w) total crude protein per dry matter, preferably at least 40% (w/w), and more preferably at least 45% (w/w) or at least 50% (w/w) of the total dry matter is soluble crude protein. The amount of soluble crude protein in a given sample can be determined by centrifugation of the sample to remove any insoluble protein components and subsequently measuring the crude protein content of the supernatant. The amount of soluble crude protein is preferably by the following procedure.

A protein concentrate solution of 1% (wt/wt) in deionized water is prepared at 20° C. and gently stirred for 30 minutes. The formation of foam must be strictly avoided. Subsequently, 1.5 ml of said solution is transferred into a 2 ml reaction tube, and the solution is centrifuged at 25, 000×g for 20 min at 4° C. 1 ml of supernatant is removed, and the crude protein content per dry matter is measured in said supernatant by the Kjeldahl method. The measurement is carried out 3 times and the average result obtained from this measurement reflects the soluble crude protein content per dry matter of the sample.

A protein concentrate of the present invention will have a soluble crude protein content of at least 40% (w/w) per dry matter as measured by the Kjeldahl method.

It is particularly preferred that the yeast protein concentrate according to the invention, which comprises a soluble crude protein content of at least 40% (w/w) per dry matter as indicated above, has a high portion of soluble crude proteins that can be precipitated by heating the concentrate. Preferably, at least 20% (w/w), and more preferably at least 25% (w/w), at least 30% (w/w), at least 35% (w/w), at least 40% (w/w), at least 45% (w/w) or at least 50% (w/w) of the soluble crude protein in the concentrate can be precipitated by heating the concentrate to 90° C. for 10 minutes. Preferably, the precipitation method is performed as follows.

A protein concentrate solution of 1% (wt/wt) in deionized water is prepared at 20° C. and gently stirred for 30 minutes. The formation of foam must be strictly avoided. Subsequently, 1.5 ml of said solution is transferred into a 2 ml reaction tube. The tube is incubated at 90° C. in a water bath for 10 minutes and then placed on ice for 10 minutes. Subsequently, the tube is centrifuged at 25,000×g for 20 min at 4° C. 1 ml of supernatant is removed, and the crude protein content per dry matter is measured in said supernatant by the Kjeldahl method.

The measurement is carried out 3 times and the average result obtained from this measurement reflects the soluble crude protein content of the sample after heat treatment. Based on this value and the total soluble protein content of the sample, one can determine the portion of the soluble crude protein that can be precipitated by heat treatment at 90° C. by the following formula:

$$100\% - \left(\frac{\text{Amount of soluble crude protein after heat incubation}}{\text{Amount of soluble crude protein}} \times 100\%\right)$$

A skilled person will have no problems to determine the portion of the crude soluble proteins that will be precipitated by heat treatment as described above.

In the protein concentrate that comprises at least 55% (w/w) total crude protein per dry matter, and preferably at least 40% (w/w) soluble crude protein, the folded proteins included preferably unfold at a temperature range between 45° C. and 83° C. Further, the protein concentrate that comprises at least 55% (w/w) total crude protein per dry matter, and preferably at least 40% (w/w) soluble crude protein, preferably comprises a total amount of free amino acids, dipeptides and tripeptides of less than 20%, more preferably less than 18%. Further, in the protein concentrate that comprises at least 55% (w/w) total crude protein per dry matter, and preferably at least 40% (w/w) soluble crude protein, preferably at least 40% of the proteins have an apparent size of more than 5 kDa.

In a preferred aspect, the yeast protein concentrates described herein are liquids having a dry matter content of at least 1%, at least 1.5%, at least 2%, at least 2.5%, at least 3%, at least 3.5%, at least 4%, at least 4.5%, or at least 5%. In another preferred aspect, the yeast protein concentrates described herein are powders having a dry matter content of at least 90%, at least 92%, at least 94%, or at least 96%.

In another aspect, the invention provides a method for preparing a protein gel, said method comprising (a) providing a liquid yeast protein concentrate as described above;
(b) heating the concentrate to a temperature of at least 55° C. to provide the protein gel.

The method comprises the provision of a liquid yeast protein concentrate. For preparing the gel, the liquid concentrate or an aliquot thereof is heated to a temperature of at least 55° C., at least 60° C., at least 65° C., at least 70° C., at least 75° C., or at least 80° C. At this temperature, the folded proteins in the liquid will denature and tangle together to form a gel.

In yet another aspect, the invention provides a method for preparing a protein gel, said method comprising (a) providing a yeast protein concentrate powder as described above;
(b) mixing the yeast protein concentrate powder with an aqueous carrier fluid;
(c) heating the mixture to a temperature of at least 55° C. to provide the protein gel.

The method starting from the dried concentrate comprises mixing the concentrate powder with an aqueous carrier fluid. The aqueous carrier fluid can be water, such as tap water, or another suitable aqueous carrier, such as a buffer solution. Reconstitution of the powder will preferably be carried out such that a solution of at least 2% (w/w), at least 5%, at least 10%, at least 15%, at least 20%, or at least 25%, is obtained. Mixing of the yeast protein concentrate powder and the aqueous carrier fluid can be performed under agitation, e.g. by stirring.

The resulting mixture is then heated to a temperature of at least 55° C., and preferably at least 60° C., at least 65° C., at least 70° C., at least 75° C., or at least 80° C. At this temperature, the folded proteins in the mixture will denature and tangle together to form the gels.

In a final aspect, the invention relates to the use of a yeast protein concentrate as described herein for the preparation of a protein-rich food or feed product. The protein-rich food product can be a dessert or pudding. Further, protein-rich food product can be a meat substitute product.

The meat substitute product can comprise additional compounds that are regularly used for the production of such products, such as starch, e.g. from rice, wheat, corn, potato, sweet potato, barley, or sorghum, and vegetable oils, such as soya, olive, rapeseed, palm, peanut, corn, flax, sunflower, safflower, or cottonseed oil.

EXAMPLES

The following examples are provided in order to illustrate the invention. It should however be understood that the scope of the invention is not limited by the examples. A skilled person will understood that several modifications can be made without deviating from the scope of the invention.

Example 1: Preparation Method Using Carbon Filtration

*Saccharomyces cerevisiae* A2W5 yeast cells were harvested from a yeast cell culture and suspended in water. The dry matter content was adjusted to 14%. The suspension had a volume of 1 L. The pH of the suspension was adjusted to pH 7.5 using NaOH.

Cell rupture was performed in a Dyno®-Mill Multi Lab Wab from Willy A. Bachofen AG (Muttenz, Switzerland) using yttria-stabilized zirconium oxide beads with a size of 0.25-0.35 mm. The flow rate was set to 7 kg/h and the rotor speed to 8 m/s. The bead filling volume was set to 65%.

The efficiency of cell rupture was confirmed by measuring the protein extraction yield using the method of Kjeldahl, J. Fresenius, Zeitschrift f. anal. Chemie (1883) 22:366.

The pH of the lysate obtained from the bead mill was adjusted to 7.6 using NaOH. Subsequently, the lysate was subjected to centrifugation for 120 minutes at 25000×g in a Heraeus Multifuge X3R. The supernatant was separated from the sediment and subjected to activated carbon filtration using an active carbon filtration cartridge (height: 5 cm, diameter: 6 cm) filled with steam activated Norit® SX Plus.

The solution obtained from activated carbon filtration was sterilized at a temperature of 130° C. for 3 seconds and subsequently spray-dried using the Mini Spray Dryer B-290 from Büchi Labortechnik GmbH (Essen, Germany) with a constant input temperature between 133-136° C. and output temperature at 93±2° C.

The powder so obtained was analyzed chemically and for the free amino acid content:

| Parameter | Amount (%) |
|---|---|
| Dry matter content | 96.3 |
| Protein content | 73 |
| RNA concentration | ≤11 |
| Free nucleotide concentration | ≤1 |
| Trehalose content | ≤2.5 |
| Salt content | 0.89 |

Free Amino Acid Analysis:

| Amino acid | Concentration % (w/w) |
|---|---|
| Ala | 3.9 |
| Arg | 0.13 |
| Asp | 0.21 |
| AspNH2 | ≤0.1 |
| Cys | 0.13 |
| Glu | 6.37 |
| Gly | 0.17 |
| His | ≤0.1 |
| Ile | 0.12 |

-continued

| Amino acid | Concentration % (w/w) |
|---|---|
| Leu | 0.15 |
| Lys | ≤0.1 |
| Met | ≤0.1 |
| Orn | 0.16 |
| Phe | ≤0.1 |
| Pro | 0.77 |
| Ser | 0.13 |
| Thr | ≤0.1 |
| Trp | ≤0.1 |
| Tyr | ≤0.1 |
| Val | 0.31 |
| total | ≤15 |

Example 2: Preparation Method Using Ultrafiltration

Figure 3:
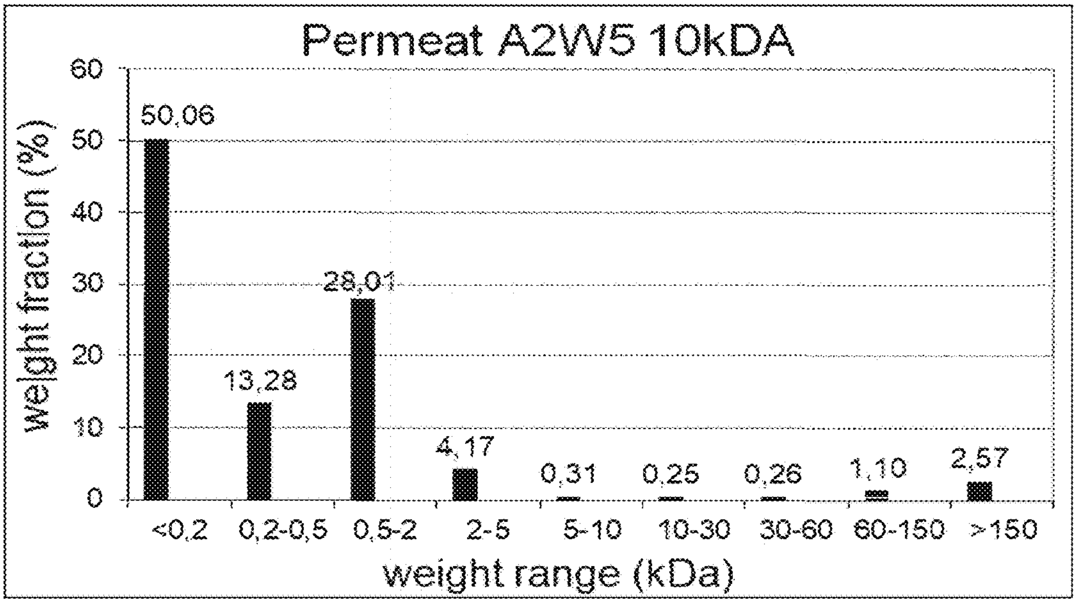
FIG. 3 shows the apparent molecular weight distribution of the ultra-filtrated permeate from Example 2 described herein below as determined by size exclusion chromatography (SEC).

The experiment described in Example 1 was repeated with the exception that an ultrafiltration was used instead of activated carbon filtration. Ultrafiltration was done with a polyethersulfone (PES) UF GR 81PP membrane having a MWCO of 10 kDa. Seven support plates were equipped with a stop disk such that 14 filters were used in total. The filter setup was washed according to the manufacturer's instructions. In the beginning the retentate flow rate was 2.3 L/min and the permeate flow rate was 0.064 L/min. After 20 min, the retentate flowed with 2.2 L/min, while the permeate flowed out with 0.054 L/min. The permeate was analyzed using Size Exclusion Chromatography (SEC). The results are shown in FIG. 3. It can be seen that only particles that were smaller than the cutoff of the membrane were able to pass. This indicates that the yeast proteins remained in the retentate and there was no significant protein loss. The solution obtained from ultrafiltration was sterilized and spray dried as described above in Example 1.

Example 3: Preparation of a Protein Gel

The powders obtained in Examples 1 and 2 were tested for their gelling properties upon reconstitution in water. For this purpose, the protein powder was dissolved in tap water to give a 20% (w/w) solution.

Figure 4:
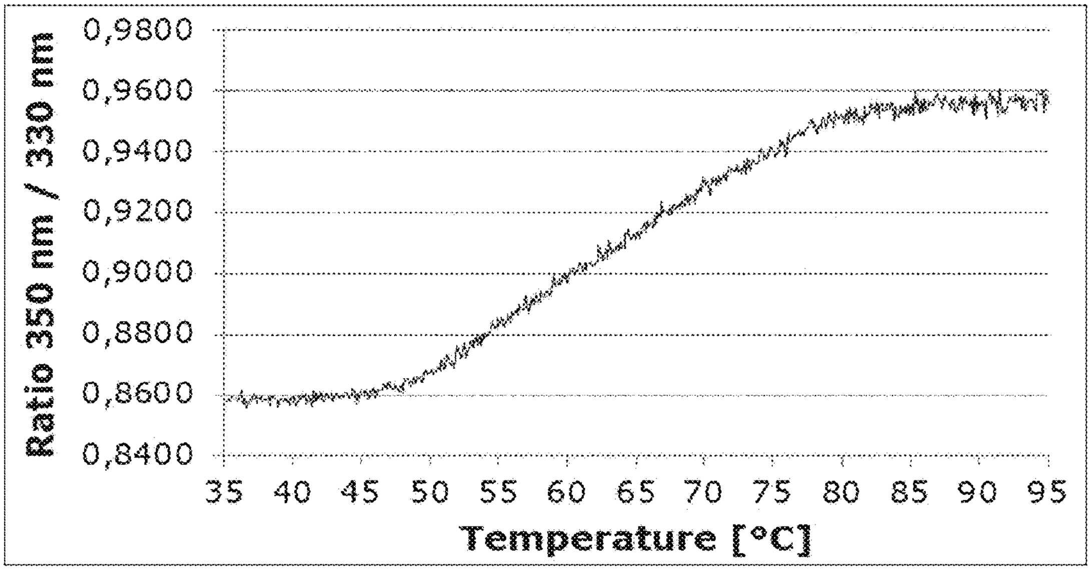
FIG. 4 shows the melting curve of the folded proteins of the protein concentrate. The dried protein concentrate was dissolved in water at 20% (w/w), and the melting curve was analysed using a Tycho NT.6 (NanoTemper Technologies GmbH, Munich).

Next, the melting temperature range of the proteins in the protein concentrate was measured between room temperature and 95° C. using a Tycho NT.6 (NanoTemper Technologies GmbH, Munich). FIG. 4 shows that the proteins inside the invented product mainly melt between 45° C. and 83° C. The protein gel was assessed by a sensory panel of at least 7 people for gel firmness and flavour profile. There was a general agreement within the panel regarding the main perception of the samples. The taste was described as salty, sweet and roasted. There was no strong yeast flavour noted by the panel. At the same time, the gel was found to be firm and resembled cooked egg white in terms of its consistency.

Example 4: Determination of the Total Crude Protein Content

A sample of the liquid yeast protein concentrate obtained after activated carbon filtration in Example 1 was analyzed for the content of total crude protein per dry matter. The liquid concentrate had a dry matter concentration of 5.3% (w/w). A 500 mg sample of the aliquot was analyzed by the Kjeldahl method using a FOSS Kjeltec-Analyser 8400 with a Kjeltec-Sampler 8420, a Tecator-Digestor Auto with a Tecator-Scrubber for the digestion step. To calculate the total crude protein content the conversion factor 6.25 was used. As a result, a total crude protein content of 70.5% (w/w) per dry matter was measured for the liquid yeast protein concentrate.

Example 5: Determination of the Soluble Crude Protein Content

A sample of the liquid yeast protein concentrate obtained after activated carbon filtration in Example 1 was diluted to a dry matter concentration of 18 (w/w) using deionized water. This solution was stirred at 20° C. for 30 minutes. A 2 ml-Eppendorf tube was filled with 1.5 ml of the diluted protein solution. The tube was centrifuged at 25,000×g for 20 min at 4° C. After centrifugation, 1 ml of the supernatant was removed from the tube and subjected to Kjeldahl protein measurement as described in Example 4. As a result, a soluble crude protein content of 61.3% (w/w) per dry matter was measured.

Example 6: Determination of Heat-Reactive Protein Portion

Another aliquot of the sample used in Example 5 having a dry matter concentration of 1% (w/w) was used as described above by stirring at 20° C. for 30 minutes. A 2 ml-Eppendorf tube was filled with 1.5 ml of the diluted protein solution. The tube was then heat-treated by putting it into a 90° C. water bath for 10 minutes. Afterwards, the tube was placed on ice for 10 minutes. Subsequently, the tube was centrifuged at 25,000×g for 20 min at 4° C. After centrifugation, 1 ml of the supernatant was removed from the tube and subjected to Kjeldahl protein measurement as described in Example 4. As a result, a soluble crude protein content after heat treatment of 32.8% (w/w) per dry matter was determined. The portion of the soluble crude protein that can be precipitated by heat is determined by the following formula:

$$100\% - \left(\frac{\text{Amount of soluble crude protein after heat incubation}}{\text{Amount of soluble crude protein}} \times 100\%\right)$$

Using the soluble crude protein content measured in Example 5 and the soluble crude protein after heat incubation measured in Example 6 in the above formula, the following is obtained:

$$100\% - (32.8\% / 61.3\% \times 100\%) = 100\% - 53.5\% = 46.5\%$$

Accordingly, the above calculation shows that 46.5% of the soluble crude protein can be precipitated by heating as described above.

The invention claimed is:

1. A method for preparing a yeast protein concentrate comprising non-denatured yeast protein molecules which can form a stable protein gel, said method comprising:

(a) providing a suspension comprising yeast cells;

(b) adjusting the pH of the suspension to a value between 7.0 and 8.0;

(c) lysing the yeast cells by mechanical means to provide a soluble fraction and an insoluble fraction;

(d) subjecting the soluble fraction to filtration to reduce the content of molecules smaller than 30 kDa and to provide the yeast protein concentrate comprising the non-denatured yeast protein;

(e) prior to performing any heating steps following step (d), drying the yeast protein concentrate obtained from the filtration in step (d) to obtain a protein concentrate powder; and wherein method steps (a)-(d) are performed at a temperature below 20° C. to result in a yeast protein concentrate that is capable of transforming into a stable protein gel upon heating to a temperature of at least 50° C.

2. The method of claim 1, wherein the method steps (a)-(d) are performed at a temperature below 15° C.

3. The method of claim 1, wherein providing the suspension comprising yeast cells comprises providing a suspension of yeast cells having a dry matter content of between about 5% to 20%.

4. The method of claim 1, further comprising washing the suspension in step (a) with a basic washing buffer prior to cell lysis.

5. The method of claim 1, wherein subjecting the soluble fraction to filtration in step (d) results in a reduction of the content of molecules smaller than 10 kDa.

6. The method of claim 1, further comprising re-adjusting the pH of the soluble fraction to a value between pH 6.5 and pH 8.5 after step (c).

7. The method of claim 1, wherein following the filtration in step (d), the yeast protein concentrate is:

(i) sterilized, and/or (ii) freeze-dried, and/or (iii) spray-dried to provide a powder.

8. The method of claim 1, wherein the yeast protein concentrate comprises at least 55% (w/w) total crude protein per dry matter.

9. The method of claim 8, wherein at least 40% (w/w) of the proteins in the yeast protein concentrate have an apparent size larger than 60 kDa.

10. The method of claim 1, wherein the resulting yeast protein concentrate is a powder having a dry matter content of at least 90%.

11. The method of claim 1, further comprising contacting the suspension of yeast cells with an RNAase enzyme prior to lysing the yeast cells.

12. A method for making a yeast protein gel, said method comprising:

(a) providing a suspension comprising yeast cells;

(b) adjusting the pH of the suspension to a value between 7.0 and 8.0;

(c) lysing the yeast cells by mechanical means to provide a soluble fraction and an insoluble fraction;

(d) subjecting the soluble fraction to filtration to reduce the content of molecules smaller than 30 kDa and to provide the yeast protein concentrate;

(e) prior to performing any heating steps following step (d), drying the yeast protein concentrate to a powder;

(f) mixing the powder with an aqueous carrier fluid to form a yeast protein mixture comprising non-denatured yeast protein molecules; and (g) heating the yeast protein mixture to a temperature of at least 50° C. to form a yeast protein gel, wherein the method steps (a)-(f) are performed at a temperature below 20° C.

13. The method of claim 12, wherein the method steps (a)-(d) are performed at a temperature below 15° C.

14. The method of claim 12, further comprising using the yeast protein gel in the preparation of a food product.

15. The method of claim 14, wherein the food product is a meat substitute product, an egg substitute product, or feed product.

16. The method of claim 12, wherein heating the yeast protein mixture to a temperature of at least 50° C. comprises heating the yeast protein mixture to a temperature of at least 55° C.

17. The method of claim 12, wherein mixing the powder with the aqueous carrier fluid comprises mixing the powder and the aqueous carrier fluid to form a 20% (w/w) solution of powder in the aqueous carrier fluid.

18. The method of claim 12, further comprising contacting the suspension of yeast cells with an RNAase enzyme prior to lysing the yeast cells.

* * * * *